United States Patent
Heser et al.

(10) Patent No.: US 12,109,078 B2
(45) Date of Patent: Oct. 8, 2024

(54) MEDICAL DEVICE SUPPORT SYSTEM INCLUDING ROTATIONAL CONTROL MECHANISM

(71) Applicant: American Sterilizer Company, Mentor, OH (US)

(72) Inventors: Michael Joseph Heser, Willoughby, OH (US); Jerime Josef Pichler, Painesville, OH (US)

(73) Assignee: American Sterilizer Company, Mentor, OH (US)

( * ) Notice: Subject to any disclaimer, the term of this patent is extended or adjusted under 35 U.S.C. 154(b) by 498 days.

(21) Appl. No.: 17/551,332

(22) Filed: Dec. 15, 2021

(65) Prior Publication Data

US 2022/0211461 A1 Jul. 7, 2022

Related U.S. Application Data

(60) Provisional application No. 63/134,263, filed on Jan. 6, 2021, provisional application No. 63/134,254, filed
(Continued)

(51) Int. Cl.
*A61B 90/50* (2016.01)
*A61B 90/00* (2016.01)
(Continued)

(52) U.S. Cl.
CPC ............. *A61B 90/50* (2016.02); *A61B 90/03* (2016.02); *A61B 90/35* (2016.02); *F21V 21/28* (2013.01);
(Continued)

(58) Field of Classification Search
CPC ... A61B 90/50; A61B 90/03; A61B 2090/035; A61B 2090/508; A61B 90/35;
(Continued)

(56) References Cited

U.S. PATENT DOCUMENTS 3,240,925 A 3/1966 Kaschke et al.
6,328,458 B1 * 12/2001 Bell .................. F21V 21/26
403/150

(Continued)

FOREIGN PATENT DOCUMENTS

| CN | 105 003 797 A | 10/2015 | |
|---|---|---|---|
| WO | WO-0145627 A1 * | 6/2001 | ............. A61B 90/50 |
| WO | 2020/159616 A1 | 8/2020 | |

OTHER PUBLICATIONS

International Search Report and Written Opinion for corresponding PCT International Application No. PCT/US2021/063448, completion date Mar. 14, 2022.

*Primary Examiner* — Tan Le
(74) *Attorney, Agent, or Firm* — Renner, Otto, Boisselle & Sklar, LLP

(57) ABSTRACT

A medical device support system including a shaft, an extension arm, and a free rotating ring. The shaft includes an elongated peripheral cavity that defines first and second contact faces at opposite peripheral ends. A hub of the extension arm is pivotably mounted for a range of at least 360 degrees rotation about a rotation axis of the shaft. The at least 360 degrees rotation range is based on a compound of a first rotation range and a second rotation range. The first rotation range is defined by a fixed stop of the hub configured to move between first and second contact faces of a radially outward protruding member of the free rotating ring. The second rotation range is defined by a radially inward protruding member of the free rotating ring configured to move between the first and second contact faces of the elongated peripheral cavity of the shaft.

20 Claims, 11 Drawing Sheets

Related U.S. Application Data on Jan. 6, 2021, provisional application No. 63/134,248, filed on Jan. 6, 2021.

(51) Int. Cl.
*A61B 90/35* (2016.01)
*F21V 21/28* (2006.01)
*A61G 12/00* (2006.01)
*F16D 49/08* (2006.01)

(52) U.S. Cl.
CPC ... *A61B 2090/035* (2016.02); *A61B 2090/508* (2016.02); *A61G 12/004* (2013.01); *F16D 49/08* (2013.01)

(58) Field of Classification Search
CPC ....... F21V 21/28; A61G 12/004; E05D 11/06; E05F 3/20; F16D 49/08
See application file for complete search history.

(56) References Cited

U.S. PATENT DOCUMENTS

| | | |
|---|---|---|
| 6,471,363 B2 | 10/2002 | Howell et al. |
| 8,070,331 B2 | 12/2011 | Gull et al. |
| 8,757,345 B2 | 6/2014 | Blank et al. |
| 8,899,834 B2 | 12/2014 | Barker et al. |
| 9,239,127 B2 | 1/2016 | Kronung |
| 9,945,498 B2 | 4/2018 | Timoszyk et al. |
| 2003/0161159 A1* | 8/2003 | Kupfer ............... F16M 11/2064 362/402 |
| 2015/0308611 A1 | 10/2015 | Oginski et al. |
| 2020/0030055 A1* | 1/2020 | Bellows ................. F16D 65/14 |
| 2020/0030056 A1 | 1/2020 | Bellows et al. |
| 2020/0030058 A1* | 1/2020 | Bellows ................. A61B 90/50 |
| 2020/0246107 A1* | 8/2020 | Moss ................... F16M 13/022 |
| 2020/0306006 A1 | 10/2020 | Bellows et al. |
| 2021/0239299 A1* | 8/2021 | Westenfelder, II ...... G02B 3/06 |
| 2021/0302808 A1* | 9/2021 | Watson ............... F21V 33/0052 |

* cited by examiner

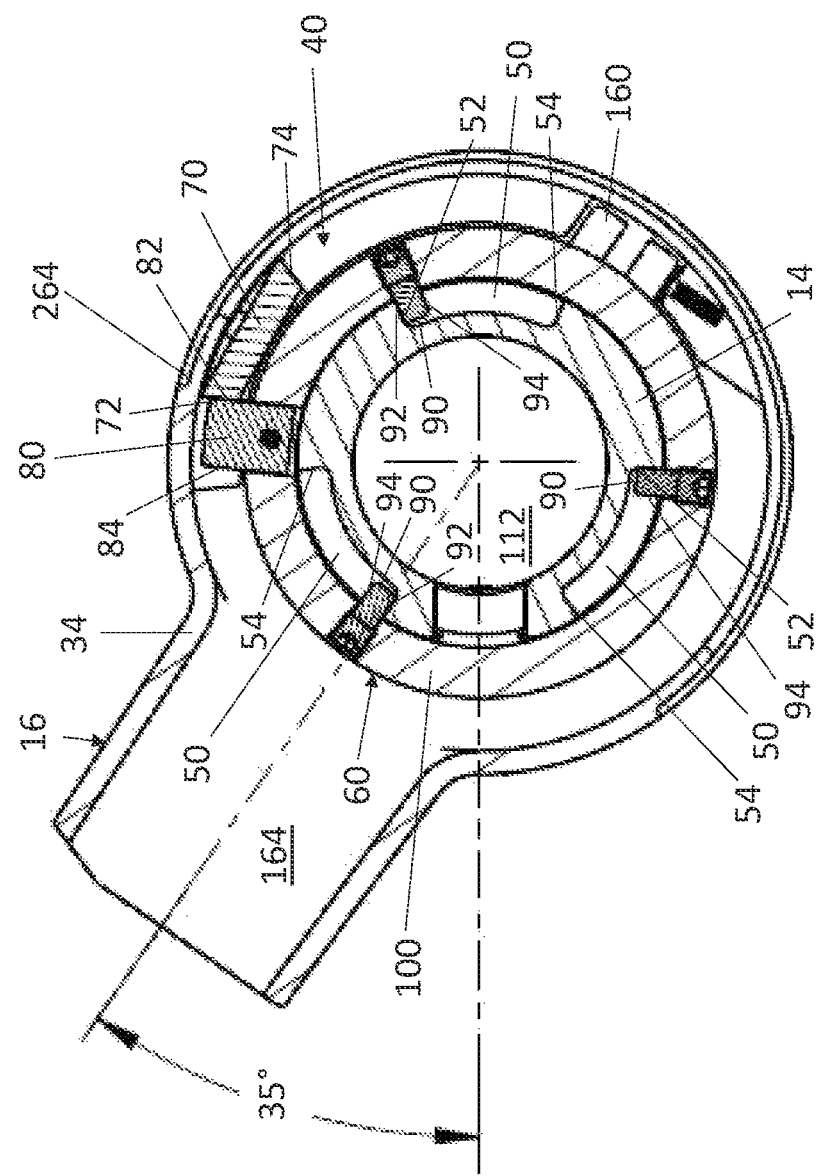

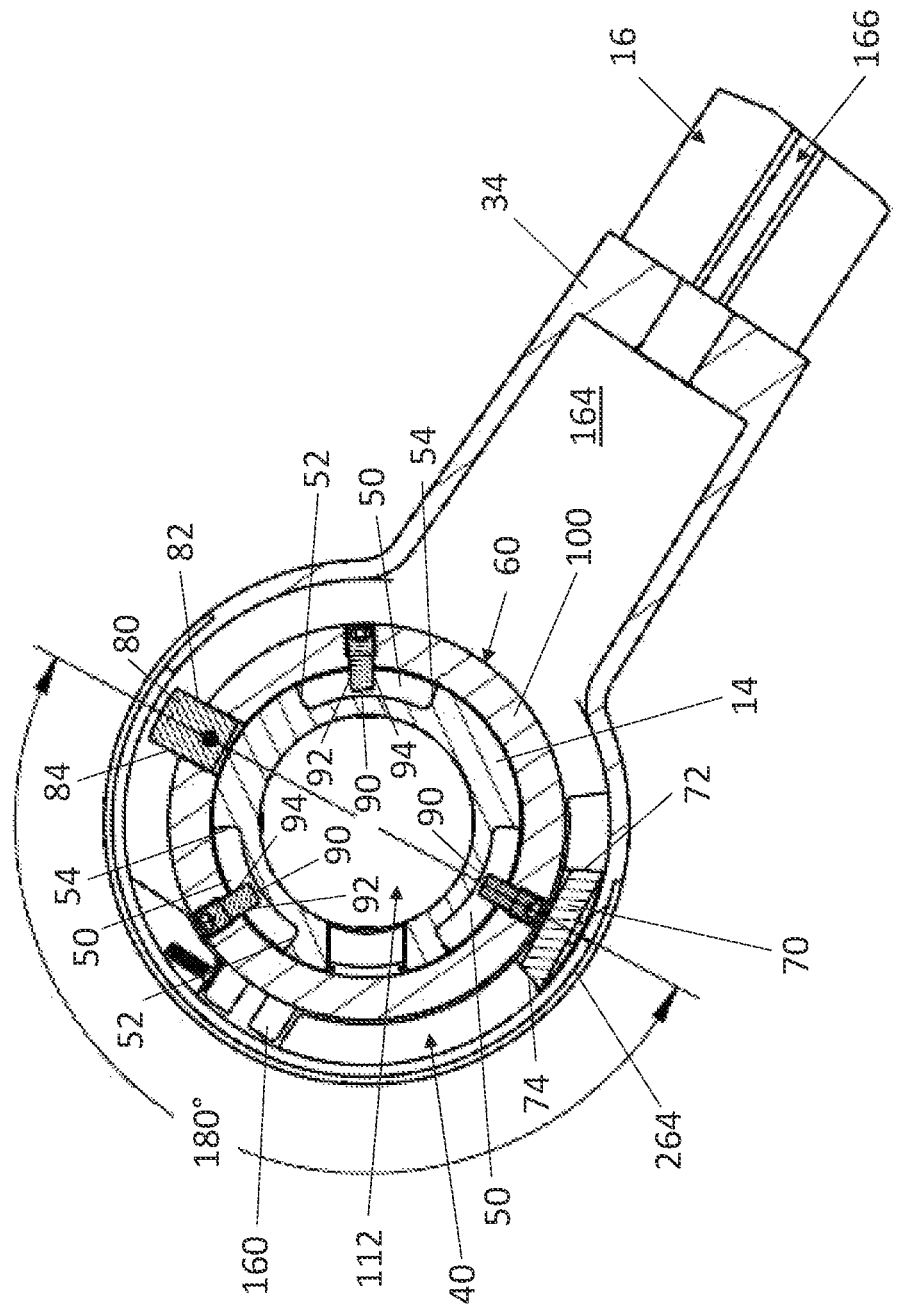
FIG. 6 CENTER

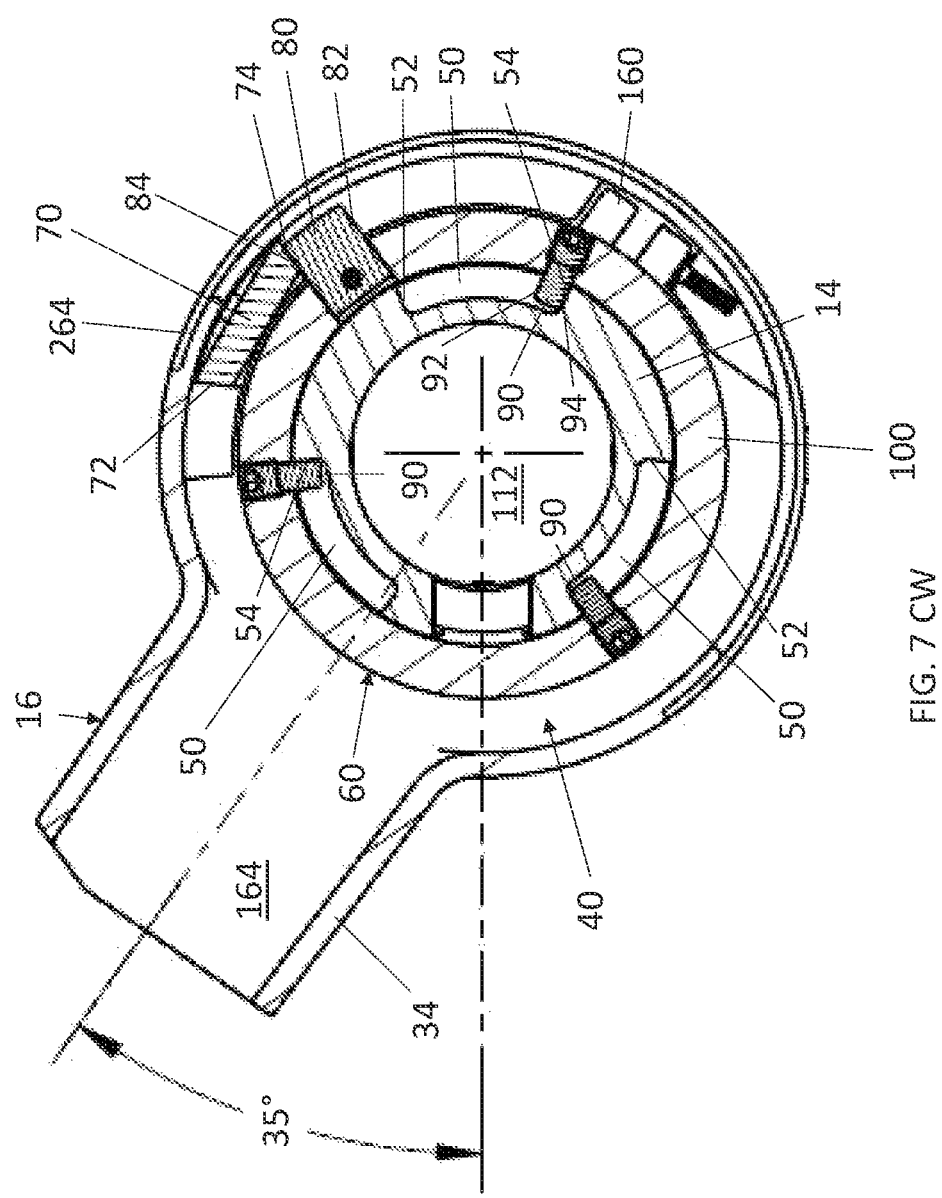

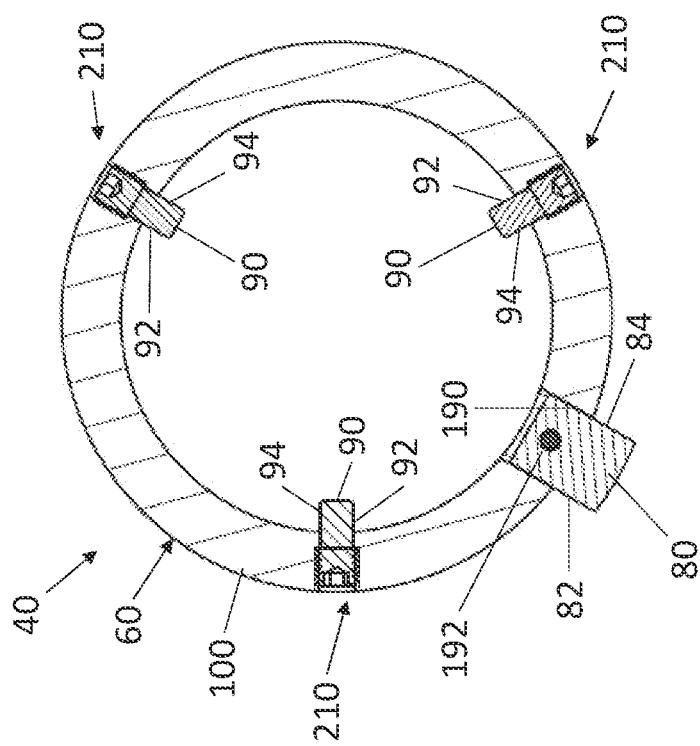
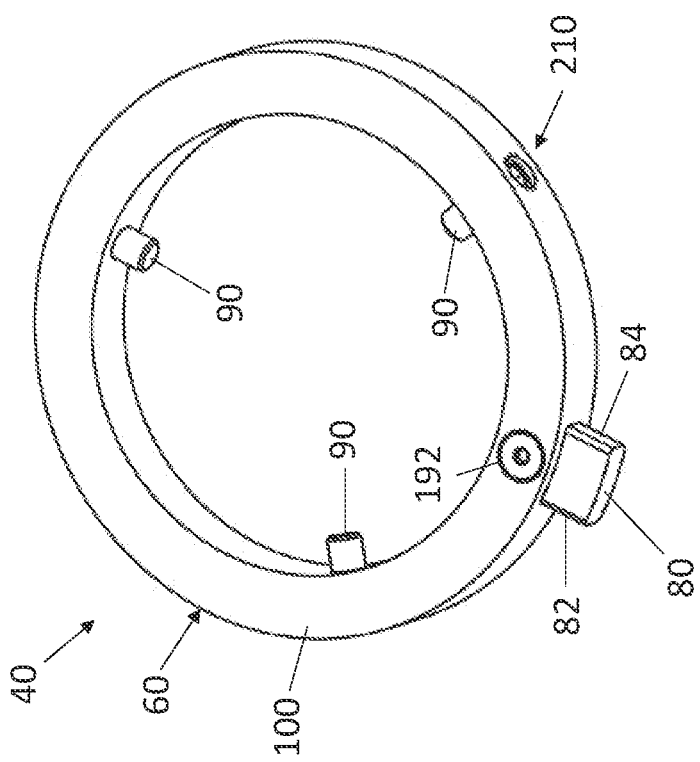
FIG. 9
FIG. 8

MEDICAL DEVICE SUPPORT SYSTEM INCLUDING ROTATIONAL CONTROL MECHANISM

RELATED APPLICATIONS

This application claims the benefit of U.S. Provisional Application No. 63/134,248, filed Jan. 6, 2021, U.S. Provisional Application No. 63/134,254, filed Jan. 6, 2021, U.S. Provisional Application No. 63/134,263, filed Jan. 6, 2021, which are hereby incorporated herein by reference in their entireties.

FIELD OF INVENTION

This application relates generally to a rotational control mechanism for a medical device suspension system or carry system for use in, for example, a hospital examination room, a clinic, a surgery room or an emergency room, and more particularly to a rotational control mechanism that simplifies rotational control of an extension arm about a shaft of the medical device support system and provides at least 360° (360 degrees) rotation of the extension arm about the shaft.

BACKGROUND

Medical device suspension systems or carry systems are used in health treatment settings such as hospital examination rooms, clinics, surgery rooms and emergency rooms. These systems may suspend or support any variety of medical devices or components including surgical lights, supply consoles, patient monitors, camera detector heads, medical instruments, ventilator systems, suction devices, among others. The systems typically include a shaft or support spindle that is suspended from the ceiling or mounted to a wall or stand, and one or more generally horizontal extension arms mounted for rotational movement about the shaft. Each extension arm typically has a hub at its proximal end mounted to the shaft for pivotable movement about the shaft, and a support at its distal end for supporting a medical device. The extension arm can be rotatably adjusted about the shaft to a desired angular position to provide appropriate access to medical devices and components associated with the arm.

It is desirable to limit the rotation of the extension arm about the shaft for example to prevent collision of medical devices at the distal ends of the arms, or to prevent undue strain on electrical or communication lines passing through the shaft and the extension arm. In most current support systems, the extension arm is equipped with a fixed feature in the hub that contacts a fixed feature on the shaft that prevents further rotation.

For rotational control mechanisms in some medical device suspension systems or carry systems, there remain various shortcomings, drawbacks, and disadvantages relative to certain applications. For example, in some systems the rotational control mechanism limits rotation of the extension arm to below 360° (360 degrees), which may limit options for some installations. Other rotational control mechanisms require multiple stacked components, which increase the volumetric footprint of the mechanisms and complicates their integration into the hub of the extension arm.

Accordingly, there remains a need for further contributions in this area of technology.

SUMMARY OF INVENTION

The application relates to a rotational control mechanism for a medical device support system, in which the rotational control mechanism enables at least 360° (360 degrees) rotation of the extension arm about the shaft, and also embodies fewer components and a smaller volumetric footprint than heretofore attained, thus simplifying and adding efficiency to the factory assembly and field service of the medical device support system.

According to one aspect of the invention, a medical device support system includes a shaft; an extension arm, and a free rotating ring. The extension arm may have a support for a medical device and a hub at its proximal end mounted to the shaft for pivotable movement about a rotation axis of the shaft. The free rotating ring may be rotatable about the rotation axis and may be movable relative to the shaft and movable relative to the hub. The shaft may include at least one elongated peripheral cavity that defines first and second contact faces at opposite peripheral ends of the cavity. The hub may be pivotably mounted for a range of at least 360° (360 degrees) rotation about the rotation axis, wherein the at least 360° (360 degrees) rotation range is based on a compound of a first rotation range and a second rotation range, wherein the first rotation range is defined by a fixed stop of the hub configured to move between first and second contact faces of a radially outward protruding member of the free rotating ring, wherein the second rotation range is defined by a radially inward protruding member of the free rotating ring configured to move between the first and second contact faces of the elongated peripheral cavity of the shaft.

Embodiments of the invention may include one or more of the following additional features separately or in combination.

The free rotating ring may be configured to prevent rotation of the hub about the rotation axis beyond the at least 360° (360 degrees) rotation range.

The hub may be pivotably mounted for at least 360° (360 degrees) rotation from a first stop to a second stop and vice versa, wherein the first stop limits counterclockwise rotation of the hub about the rotation axis and the second stop limits clockwise rotation of the hub about the rotation axis.

The first stop may include the fixed stop of the hub in engagement with the first contact face of the radially outward protruding member of the free rotating ring, and the radially inward protruding member of the free rotating ring in engagement with the first contact face of the elongated peripheral cavity of the shaft.

The second stop may include the fixed stop of the hub in engagement with the second contact face of the radially outward protruding member of the free rotating ring, and the radially inward protruding member of the free rotating ring in engagement with the second contact face of the elongated peripheral cavity of the shaft.

The radially outward protruding member of the free rotating ring and the radially inward protruding member of the free rotating ring may lie in the same plane and the plane may be perpendicular to the rotation axis.

The fixed stop of the hub and the radially inward protruding member of the free rotating ring may lie in the same plane and the plane may be perpendicular to the rotation axis.

The radially outward protruding member of the free rotating ring may include a tab, and the first and second contact faces of the radially outward protruding member of the free rotating ring may be on opposite peripheral sides of the tab.

The free rotating ring may include a ring member and the tab may be secured within a radial opening in the ring member.

The radially inward protruding member of the free rotating ring may have first and second contact faces on opposite sides thereof, and the second rotation range may be defined by movement of the radially inward protruding member between a location at which the first contact face of the radially inward protruding member engages the first contact face of the elongated peripheral cavity of the shaft and a location at which the second contact face of the radially inward protruding member engages the second contact face of the elongated peripheral cavity of the shaft.

The free rotating ring may include a ring member, and the radially inward protruding member of the free rotating ring may include a fastener threaded into an opening in the ring member, and the fastener may protrude radially inward relative to an inner diameter of the ring member.

The at least one elongated peripheral cavity may include a plurality of elongated peripheral cavities.

The radially inward protruding member of the free rotating ring may include a plurality radially inward protruding members that move within the respective plurality of elongated peripheral cavities.

The plurality of elongated peripheral cavities may be evenly spaced about the rotation axis of the shaft.

The shaft may have an axial hollow and a radial aperture and the free rotating ring may be positioned to allow passage of electrical and communication lines through the axial hollow, through the free rotating ring, through the radial aperture, and into a longitudinally extending cavity in the extension arm.

The hub of the extension arm may include upper and lower pivot bearings configured to pivotably engage the hub with the shaft, and a radial opening may be positioned axially between the upper and lower pivot bearings, and the free rotating ring may be positioned to allow passage of the electrical and communication lines between the upper and lower pivot bearings, through the radial opening of the hub, and into the longitudinally extending cavity in the extension arm.

According to another aspect of the invention, a medical device support system includes a shaft, an extension arm, and a free rotating ring. The extension arm may have a support for a medical device and a hub at its proximal end mounted to the shaft for pivotable movement about a rotation axis of the shaft. The free rotating ring may be rotatable about the rotation axis and may be movable relative to the shaft and movable relative to the hub. The shaft may include at least one elongated peripheral cavity that defines first and second contact faces at opposite peripheral ends of the cavity. The hub may be pivotably mounted for a range of at least 360° (360 degrees) rotation about the rotation axis from a first stop to a second stop and vice versa, wherein the first stop limits counterclockwise rotation of the hub about the rotation axis and the second stop limits clockwise rotation of the hub about the rotation axis. The first stop may include a radially inward protruding member of the free rotating ring in engagement with the first contact face of the elongated peripheral cavity of the shaft, and the second stop may include the radially inward protruding member of the free rotating ring in engagement with the second contact face of the elongated peripheral cavity of the shaft.

Embodiments of the invention may include one or more of the following additional features separately or in combination.

The hub may include a fixed stop movable between first and second contact faces of a radially outward protruding member of the free rotating ring.

The first stop may include the fixed stop of the hub in engagement with the first contact face of the radially outward protruding member of the free rotating ring, and the second stop may include the fixed stop of the hub in engagement with the second contact face of the radially outward protruding member of the free rotating ring.

According to another aspect of the invention, there is provided a method of rotating an extension arm about a shaft of a medical device support system, the extension arm having a support for a medical device and a hub at its proximal end mounted to the shaft for pivotable movement about a rotation axis of the shaft, wherein a free rotating ring is rotatable about the rotation axis and is movable relative to the shaft and movable relative to the hub, and wherein the shaft includes at least one elongated peripheral cavity that defines first and second contact faces at opposite peripheral ends of the cavity, the method including rotating the hub over a range of at least 360° (360 degrees) about the rotation axis, wherein the at least 360° (360 degrees) rotation range is based on a compound of movement over a first rotation range and movement over a second rotation range, wherein movement over the first rotation range includes moving a fixed stop of the hub between first and second contact faces of a radially outward protruding member of the free rotating ring, and wherein movement over the second rotation range includes moving a radially inward protruding member of the free rotating ring between the first and second contact faces of the elongated peripheral cavity of the shaft.

The following description and the annexed drawings set forth certain illustrative embodiments of the invention. These embodiments are indicative, however, of but a few of the various ways in which the principles of the invention may be employed. Other objects, advantages and novel features according to aspects of the invention will become apparent from the following detailed description when considered in conjunction with the drawings.

BRIEF DESCRIPTION OF THE DRAWINGS

The annexed drawings, which are not necessarily to scale, show various aspects of the invention.

FIG. 5 shows a top cross section view of the rotational control mechanism of the medical device support system of FIG. 1, showing a maximum counterclockwise position of a free rotating ring of the rotational control mechanism.

FIG. 6 shows a top cross section view of the rotational control mechanism of the medical device support system of FIG. 1, showing a mid-rotation position of a free rotating ring of the rotational control mechanism.

FIG. 7 shows a top cross section view of the rotational control mechanism of the medical device support system of FIG. 1, showing a maximum clockwise position of a free rotating ring of the rotational control mechanism, where the rotation is at least 360° (360 degrees) rotation from that shown in FIG. 5.

FIG. 8 is an isometric view of a free rotating ring of the rotational control mechanism, showing a floating stop and pins therein.

FIG. 9 is a top cross section view of the FIG. 8 free rotating ring, showing a floating stop and pins therein.

DETAILED DESCRIPTION

Figure 1:
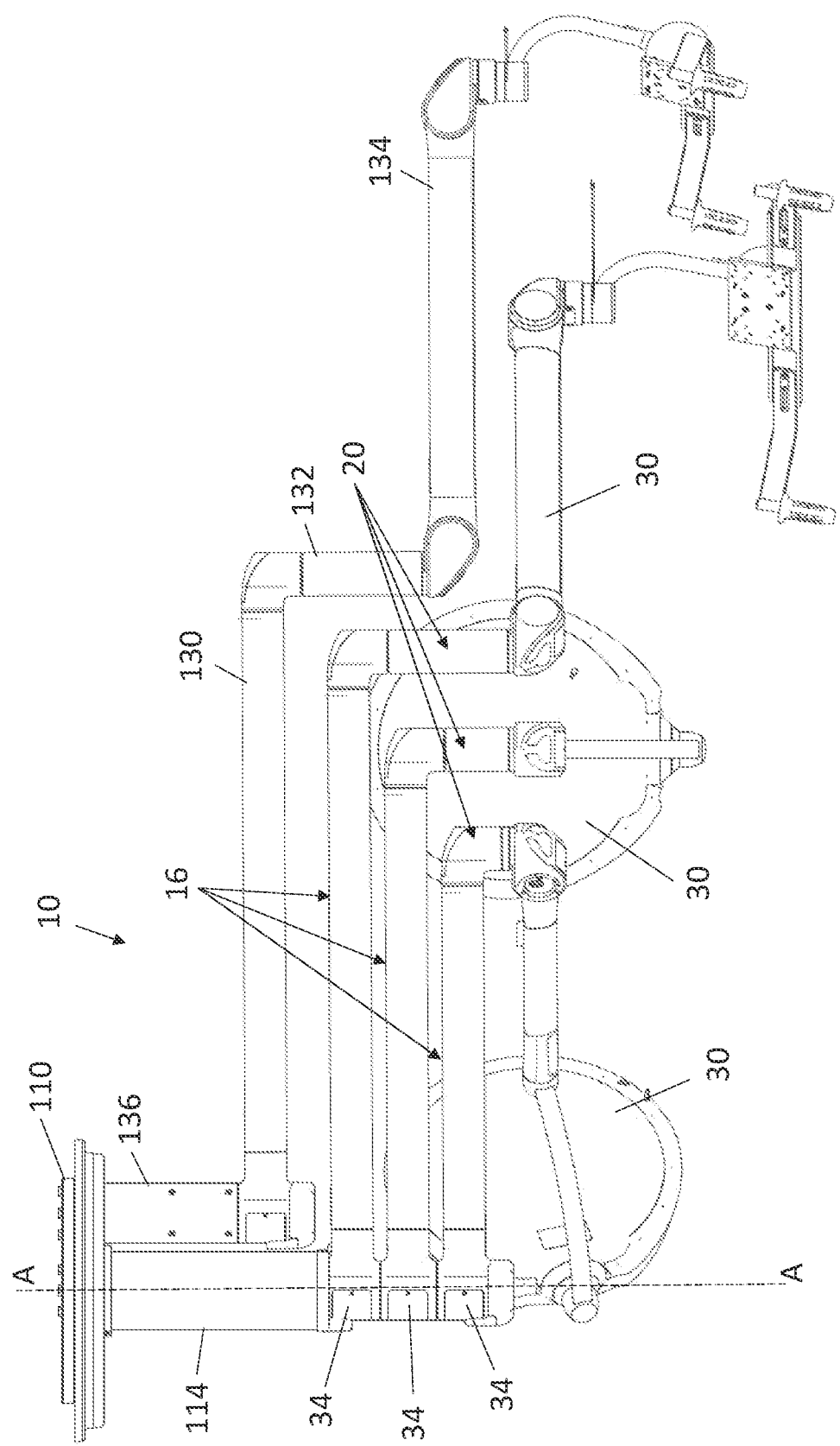
FIG. 1 is a front elevational view of a medical device support system in accordance with an embodiment of the invention.

While the present invention can take many different forms, for the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications of the described embodiments, and any further applications of the principles of the invention as described herein, are contemplated as would normally occur to one skilled in the art to which the invention relates.

FIGS. 1-5 show a medical device support system 10 that includes a shaft 14, at least one extension arm 16 having a support 20 for a medical device 30 and a hub 34 at its proximal end mounted to the shaft 14 for pivotable movement about a rotation axis A-A of the shaft 14, and a rotational control mechanism 40 integrated into the hub 34 for controlling the amount of rotation of the extension arm 16 about the shaft 14. The shaft 14 includes at least one elongated peripheral cavity 50 that defines first and second contact faces 52, 54 at opposite peripheral ends of the cavity 50. The rotational control mechanism 40 includes a free rotating ring 60, a fixed stop 70 connected to a wall of the hub 34, and a radially outward protruding member 80 and at least one radially inward protruding member 90 protruding respectively radially outward and radially inward relative to a ring member 100 of the free rotating ring 60. The free rotating ring 60 is rotatable about the rotation axis A-A and is movable relative to the shaft 14 and movable relative to the hub 34. The hub 34 is pivotably mounted for a range of at least 360° (360 degrees) rotation about the rotation axis A-A. The at least 360° (360 degrees) rotation range is based on a compound of a first rotation range and a second rotation range. The first rotation range is defined by the fixed stop 70 of the hub 34 being configured to move between first and second contact faces 82, 84 of the radially outward protruding member 80 of the free rotating ring 60. The second rotation range is defined by the radially inward protruding member 90 of the free rotating ring 60 being configured to move between the first and second contact faces 52, 54 of the elongated peripheral cavity 50 of the shaft 14. As will be described in greater detail below, the rotational control mechanism 40 simplifies rotational control of the extension arm 16 about the shaft 14 and provides a range of at least 360° (360 degrees) rotation of the extension arm 16 about the rotation axis A-A.

Figure 2:
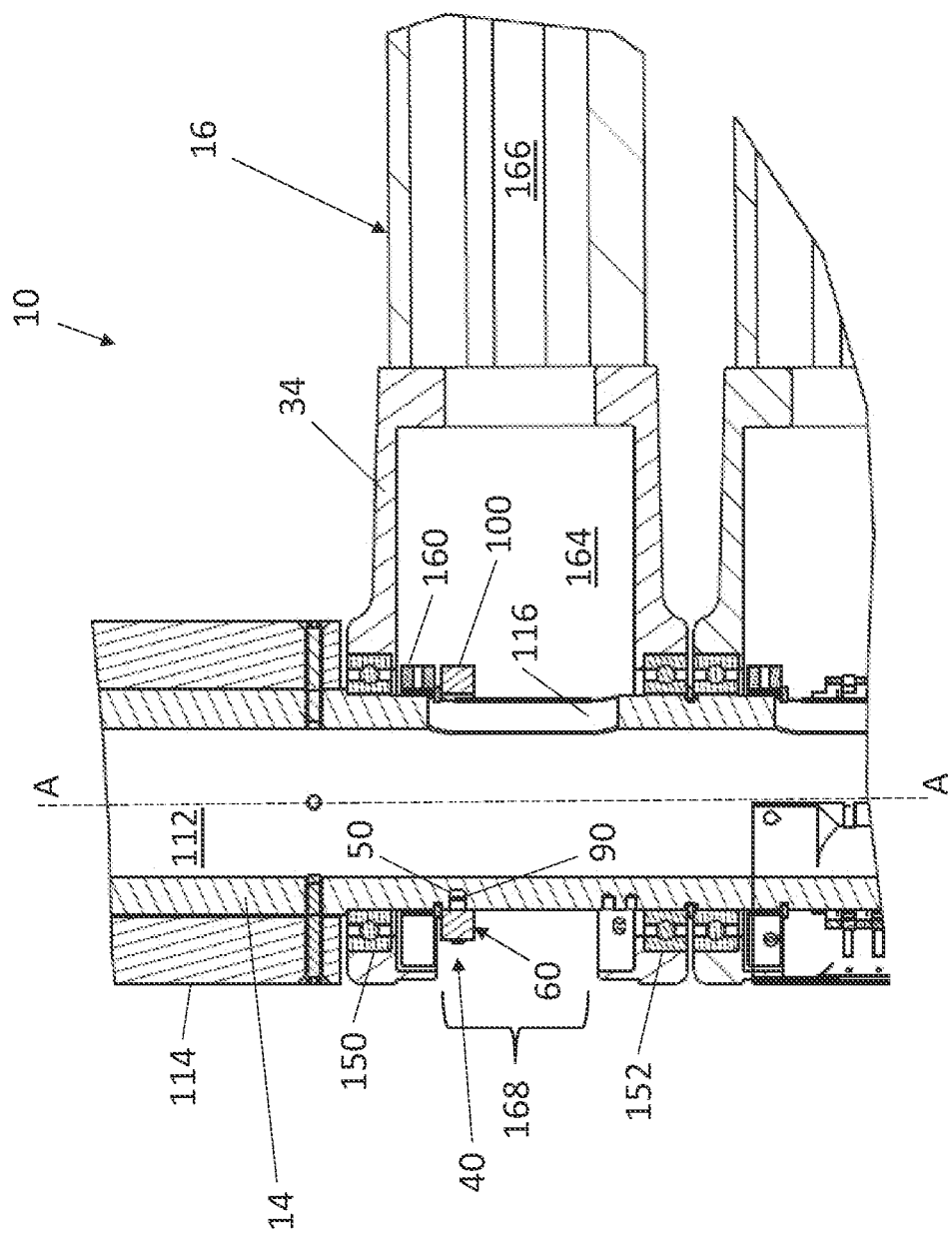
FIG. 2 is a cross section view of a shaft and extension arm hub connection of the FIG. 1 medical device support system, showing a rotational control mechanism in accordance with an embodiment of the invention.
Figure 4:
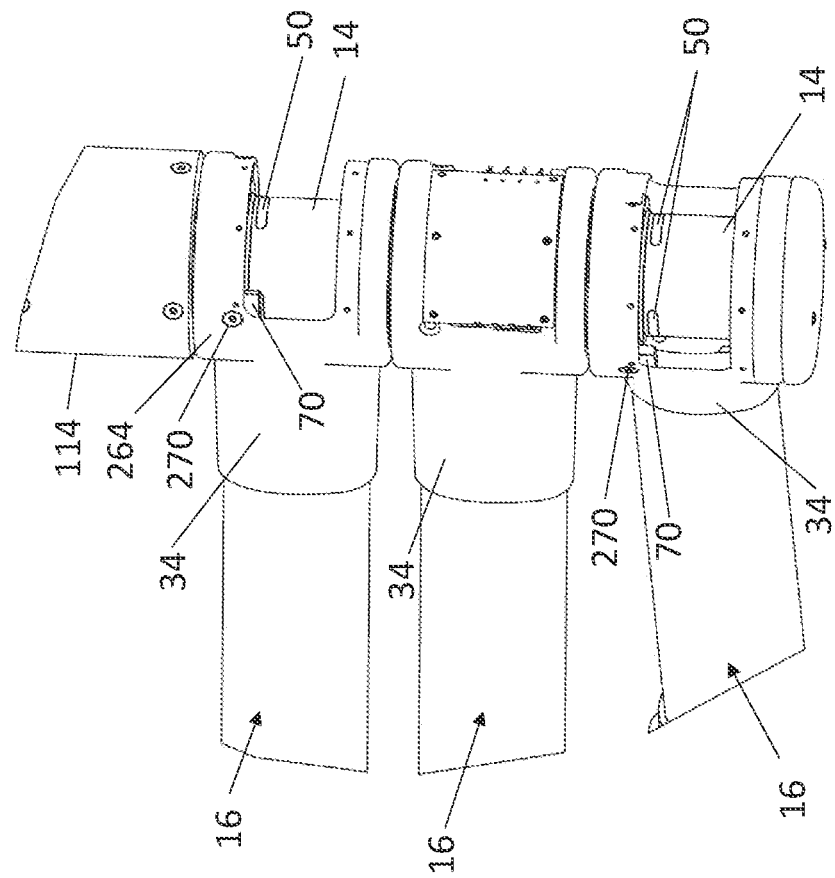
FIG. 4 is a view similar to the FIG. 3 view but omitting a free rotating ring on the shaft to show elongated peripheral cavities in the shaft.
Figure 3:
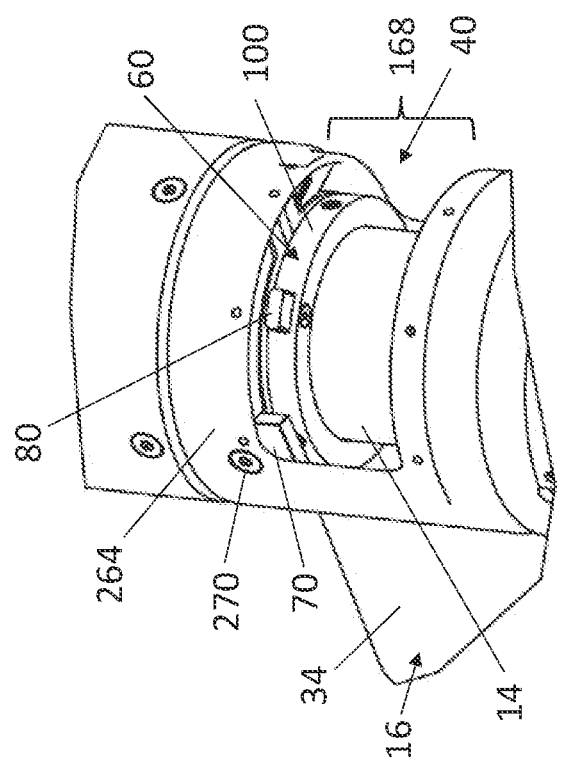
FIG. 3 is a bottom isometric view of the FIG. 2 shaft and extension arm hub connection, showing a free rotating ring on the shaft.

Referring to FIGS. 1 and 2, the illustrative medical device support system 10 is a suspension type carrying support system for use in a hospital examination room, a clinic, a surgery room, an emergency room, among others. The shaft 14 extends along an axis A-A, which also represents the rotation axis A-A of the shaft 14 about which the extension arm 16 pivots. The shaft 14 may be fixed to a ceiling support 110 to remain stationary relative to the ceiling. It will be appreciated, of course, that the medical device support system 10 may have any suitable suspension or carrying structure and that the shaft 14 may be attached to a ceiling as shown, or to a wall, floor, movable cart, or a combination of the foregoing. The shaft 14 of the medical device support system 10 has a cylindrical shape in axial cross section and defines an axial hollow 112 and radial aperture 116 therein, and extends vertically downward from the ceiling support 110. A column section 114 surrounds an upper portion of the shaft 14. The axial hollow 112 and the column section 114 house upper portions of accessory and service lines such as power cables for surgical lights and other power requirements, control wiring for control electronics, optical fibers for data communication, and/or tubing for irrigation, suction, etc. A plurality of extension arms 16, three in the illustrative embodiment, are mounted for rotatable movement to the shaft 14 and extend laterally outward from the shaft 14. In the FIG. 1 embodiment, the extension arms 16 extend horizontally, or perpendicularly, relative to the shaft 14. An additional extension arm 130, support arm 132, and medical device 134 may be pivotably mounted to a separate central shaft 136 radially offset from the central shaft 14.

Figure 11:
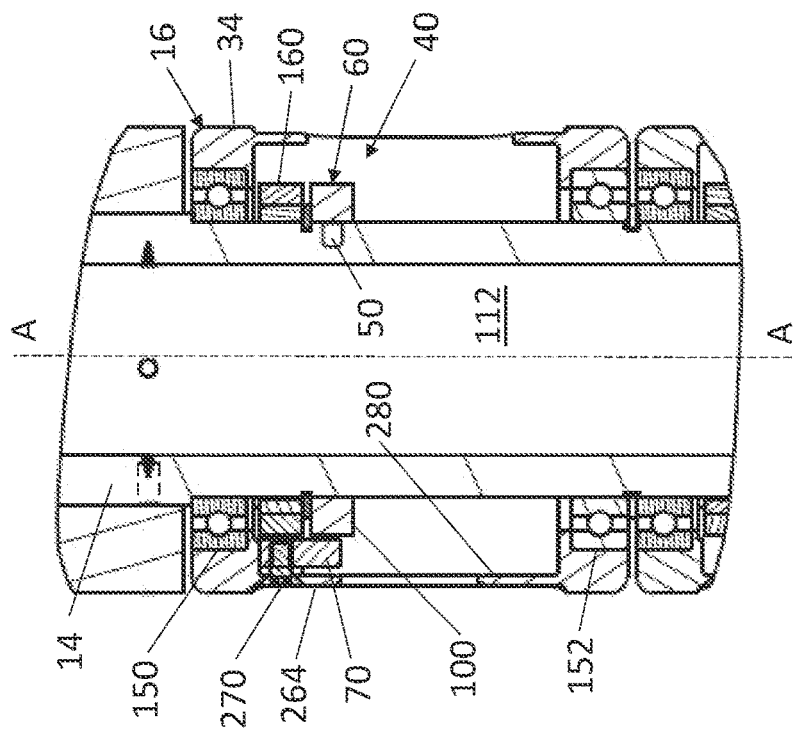
FIG. 11 is an isometric cutaway view of the FIGS. 2-3 shaft and extension arm hub connection, showing a fixed stop of the rotational control mechanism mounted to a hub of the extension arm.
Figure 12:
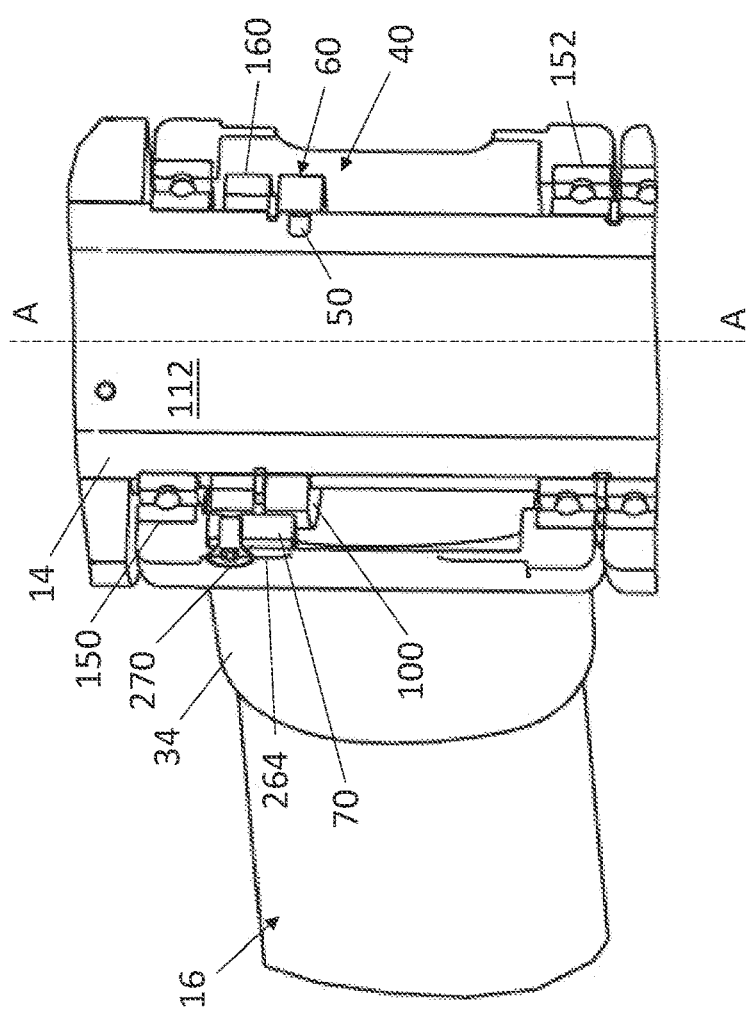
FIG. 12 is a cross section view of the FIG. 11 shaft and extension arm hub connection, showing the fixed stop in greater detail.

The hub 34 is located at the proximal end of the extension arm 16. In the illustrative embodiment, to aid in the pivotable movement of the extension arm 16 about the shaft 14, each extension arm hub 34 may include upper and lower bearing mounts 150, 152, shown in FIGS. 2, 11 and 12, that house respective upper and lower pivot bearings mounted to the shaft 14. Any suitable pivot bearings may be used to enable the relative rotational movement between the extension arm 16 and the shaft 14, including for example ball bearings, sleeve bearings, bushings, rotary joints and/or swivel joints. A brake assembly 160 may be secured in the hub 34 for rotation therewith to selectively increase and decrease a frictional braking force to the shaft 14. In the illustrative embodiment, the brake assembly 160 is positioned below the upper bearing 150 and above the free rotating ring 60. Each hub 34 provides a radial opening 164 positioned axially between the upper and lower pivot bearings 150, 152 for routing accessory and service lines from the axial hollow 112 and/or the upper column section 114 through the radial aperture 116 and to a longitudinally extending cavity 166 of the extension arm 16, and/or vice versa. Each hub 34 is also provided with an access opening 168 to enable access to the shaft 14, the rotational control mechanism 40, the upper and lower pivot bearings 150, 152, the brake assembly 160, accessory and service lines, and/or other components within the hub 34. A suitable brake assembly 160 and access opening 168 for the illustrative embodiment are described in U.S. patent application Ser.

Nos. 16/517,703; 16/517,704; 16/517,707; and 16/517,708, which are incorporated by reference for all purposes as if fully set forth herein.

Reference is now made to FIGS. 5-7, which show greater detail of the rotational control mechanism 40. The rotational control mechanism 40 is made up of a combination of components from the hub 34 of the extension arm 16, the free rotating ring 60, and the shaft 14. The hub 34 includes the fixed stop 70. The free rotating ring 60 includes the radially outward protruding member 80, at least one radially inward protruding member 90, three such radially inward protruding members 90 in the illustrative embodiment, and the ring member 100. The shaft 14 includes at least one elongated peripheral cavity 50, three such elongated peripheral cavities 50 in the illustrative embodiment. In FIGS. 5-7, it can be seen that the extension arm 16 and its hub 34 and the fixed stop 70 of the rotational control mechanism 40 are movable relative to the shaft 14. As is also apparent from FIGS. 5-7, the free rotating ring 60 including its protruding members 80, 90, is movable relative to the shaft 14 and movable relative to the hub 34 and the fixed stop 70.

Each of the components of the rotational control mechanism 40 provides contact faces, that is, faces for abutting engagement, to control the amount of rotation of the extension arm 16 about the rotation axis A-A of the shaft 14. The fixed stop 70 has first and second contact faces 72, 74 on opposite peripheral ends of the fixed stop 70. The radially outward protruding member 80 has first and second contact faces 82, 84 on opposite peripheral ends of the radially outward protruding member 80. Each radially inward protruding member 90 has first and second contact faces 92, 94 on opposite peripheral ends of the radially inward protruding member 90. Each cavity 50 defines first and second contact faces 52, 54 at opposite peripheral ends of the cavity 50. In this way, the rotational control mechanism 40 embodies fewer components and a smaller volumetric footprint than heretofore attained and simplifies and adds efficiency to the factory assembly and field service of the medical device support system 10.

The free rotating ring 60 is configured to prevent rotation of the hub 34 about the rotation axis A-A beyond the at least 360° (360 degrees) rotation range. The hub 34 is pivotably mounted for at least 360° (360 degrees) rotation from a first stop shown in FIG. 5 to a second stop shown in FIG. 7, and vice versa. As shown in FIG. 5, the first stop limits counterclockwise rotation of the hub 34 about the rotation axis A-A. Thus, the first stop defines the most counterclockwise rotation the hub 34 and thus the extension arm 16 obtain about the shaft 14. In FIG. 5, the first stop, or most counterclockwise rotation of the extension arm 16, positions the extension arm 16 at 35° (35 degrees) relative to a horizontal line across the page. As shown in FIG. 7, the second stop limits clockwise rotation of the hub 34 about the rotation axis A-A. Thus, the second stop defines the most clockwise rotation the hub 34 and associated extension arm 16 obtain about the shaft 14. In FIG. 7, the second stop, or most clockwise rotation of the extension arm 16, positions the extension arm 16 at 35° (35 degrees) relative to the horizontal line across the page. As is apparent from FIGS. 5 and 7, the rotation of the extension arm 16 and its hub 34 about the shaft 14 is 360° (360 degrees), which, going from FIG. 5 to FIG. 7, is 360° (360 degrees).

Two abutting engagements form the first or most counterclockwise stop and two abutting engagements form the second or most clockwise stop. Referring to FIG. 5, the first stop includes the fixed stop 70 of the hub 34 in engagement with the first contact face 82 of the radially outward protruding member 80 of the free rotating ring 60, and the radially inward protruding member 90 of the free rotating ring 60 in engagement with the first contact face 52 of the elongated peripheral cavity 50 of the shaft 14. Referring to FIG. 7, the second stop includes the fixed stop 70 of the hub 34 in engagement with the second contact face 84 of the radially outward protruding member 80 of the free rotating ring 60, and the radially inward protruding member 90 of the free rotating ring 60 in engagement with the second contact face 54 of the elongated peripheral cavity 50 of the shaft 14.

The rotational control mechanism 40 facilitates the at least 360° (360 degrees) rotation range based on a compound of a first rotation range and a second rotation range. As previously noted, the first rotation range is defined by the fixed stop 70 of the hub 34 being configured to move between the first and second contact faces 82, 84 of the radially outward protruding member 80 of the free rotating ring 60. In the illustrated embodiment, the angular span between the first and second contact faces 72, 74 of the fixed stop 70 is about 35-degrees. The radially outward protruding member 80 has an angular span of about 15-degrees between its first and second contact faces 82, 84. With reference to FIG. 5, and assuming that the free rotating ring 60 remains idle with rotation of the hub 34, the first rotation range is defined by movement of the fixed stop 70 between a location shown in FIG. 5 at which the first contact face 72 of the fixed stop 70 engages the first contact face 82 of the radially outward protruding member 80 and a location at which the second contact face 74 of the fixed stop 70 engages the second contact face 84 of the radially outward protruding member 80. In other words, and again with reference to FIG. 5 and assuming the free rotating ring 60 remains stationary, the first rotation range is defined by the fixed stop 70 moving from the position shown in FIG. 5 where the first contact face 72 abuttingly engages the first contact face 82, to a position where the second contact face 74 abuttingly engages the second contact face 84; that is, in FIG. 5, the fixed stop 70 moves from the first contact face 82 of the radially outward protruding member 80 (or right side thereof in FIG. 5) clockwise to the second contact face 84 of the radially outward protruding member 80 (or left side thereof in FIG. 5). In the FIGS. 5-7 embodiment, the first rotation range of the rotational control mechanism 40 is approximately 310° (310 degrees) (360 minus 35 minus 15).

The second rotation range is defined by the radially inward protruding member 90 of the free rotating ring 60 being configured to move between the first and second contact faces 52, 54 of the elongated peripheral cavity 50 of the shaft 14. In the illustrated embodiment, the angular span between the first and second contact faces 52, 54 of the elongated peripheral cavity 50 is about 55-degrees. The radially inward protruding member 90 has an angular span of about 5-degrees between its first and second contact faces 92, 94. With continued reference to FIG. 5, it is assumed that the hub 34 has rotated clockwise the first rotation range, that is, the second contact face 74 is in abutting engagement with the second contact face 84, and thus continued clockwise rotation of the hub 34 causes the hub 34 and free rotating ring 60 to rotate together clockwise in unison. The second rotation range is defined by movement of the radially inward protruding member 90 between a location at which the first contact face 92 of the radially inward protruding member 90 engages the first contact face 52 of the elongated peripheral cavity 50 of the shaft 14 and a location shown in FIG. 7 at which the second contact face 94 of the radially inward protruding member 90 engages the second contact face 54 of the elongated peripheral cavity 50 of the shaft 14. In other words, and again with reference to FIG. 5 and assuming the second contact face 74 is in abutting engagement with the second contact face 84, the second rotation range is defined by the radially inward protruding member 90 moving from the position shown in FIG. 5 where the first contact face 92 abuttingly engages the first contact face 52, to a position where the second contact face 94 abuttingly engages the second contact face 54; that is, in FIG. 5, the radially inward protruding member 90 moves from the first contact face 52 of the elongated peripheral cavity 50 clockwise to the second contact face 54 of the elongated peripheral cavity 50. In the FIGS. 5-7 embodiment, the second rotation range of the rotational control mechanism 40 is approximately 50° (50 degrees) (55 minus 5).

As will be appreciated, in operation the first and second rotation ranges usually will not be completed in serial fashion but rather at least partially in parallel fashion. This is illustrated in FIG. 6, for example, where the hub 34, relative to the FIG. 5 position, has been rotated clockwise about the shaft 14 about 180° (180 degrees) to a position at which the fixed stop 70 has reached 180° (180 degrees) from the radially outward protruding member 80, that is, the middle of the first rotation range, and the radially inward protruding member 90 has reached the middle of the elongated peripheral cavity 50, that is, the middle of the second rotation range. It will be appreciated that the movement of the fixed stop 70 between the first and second contact faces 82, 84 of the radially outward protruding member 80, and the movement of the radially inward protruding member 90 between the first and second contact faces 52, 54 of the elongated peripheral cavity 50, will vary depending on the friction between the respective rotating sliding surfaces of the shaft 14, the hub 34, and the free rotating ring 60. Thus, while FIG. 5 shows the start of the first and second rotation ranges, and FIG. 7 shows the completion of the first and second rotation ranges, what occurs between the start and completion of the first and second rotation ranges will depend on the friction between the rotating sliding surfaces.

It will be appreciated that the rotational control mechanism 40 can provide a greater than 360° (360 degrees) rotation range by adjusting any of its components, for example the width (angular span) of any of the elongated peripheral cavity 50, the fixed stop 70, the radially outward protruding member 80, and/or the radially inward protruding member 90. As an example, in the case where the fixed stop 70 is 1.0° (1.0 degree) smaller in width in FIGS. 5-7, for example 34 degrees in width, then in FIG. 5, the first stop, or most counterclockwise rotation of the extension arm 16, positions the extension arm 16 at 34° (34 degrees) relative to a horizontal line across the page, and in FIG. 7, the second stop, or most clockwise rotation of the extension arm 16, positions the extension arm 16 at 35° (35 degrees) relative to the horizontal line across the page. The total rotation of the extension arm 16 and its hub 34 about the shaft 14 is then 361° (361 degrees), where the first rotation range is 311° (311 degrees) (360 minus 34 minus 15) and the second rotation range is 50° (50 degrees) (55 minus 5).

In exemplary embodiments, the angular span between the first and second contact faces 72, 74 (e.g., width of fixed stop 70) may be in a range from about 1-degree to about 120-degrees, even more particularly between 1-degree and 60-degrees, such as about 35-degrees in the illustrated embodiment. In exemplary embodiments, the radially outward protruding member 80 may have an angular span in a range from about 1-degree to about 45-degrees, even more particularly between 1-degree and 20-degrees, such as about 15-degrees in the illustrated embodiment. In exemplary embodiments, the elongated peripheral cavity 50 forms an arcuate segment defined by an angular span between the opposite first and second contact faces 52, 54 that may be in a range from about 1-degree to about 180-degrees (180 degrees, for example, where there is only one such cavity rather than three), and even more particularly from about 10-degrees to about 60-degrees, such as about 55-degrees in the illustrated embodiment. In exemplary embodiments, the radially inward protruding member 90 may have an angular span in a range from about 1-degree to about 45-degrees, even more particularly between 1-degree and 20-degrees, such as about 5-degrees in the illustrated embodiment. In exemplary embodiments, the at least 360-degrees range provided by the rotational control mechanism 40 may be in a range from 360-degrees to less than 720-degrees, more particularly from 360-degrees to 540-degrees, and even more particularly from 360-degrees to 450-degrees, such as about 360-degrees in the illustrated embodiment.

Figure 10:
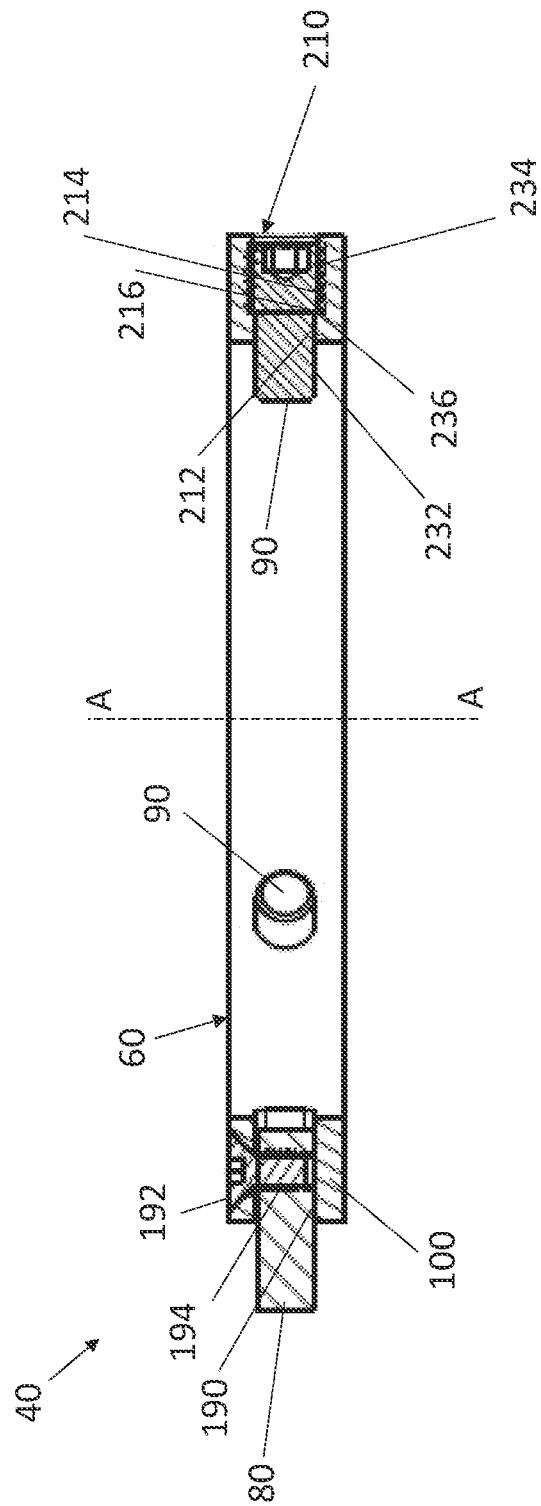
FIG. 10 is a side cross section view of the FIG. 8 free rotating ring, showing a floating stop and pins therein.

FIGS. 8-10 show greater detail of the free rotating ring 60 of the rotational control mechanism 40. The free rotating ring 60 includes the ring member 100. The inner diameter of the ring member 100 is slightly larger than the outer diameter of the shaft 14 to enable the ring member 100 to slidably rotate about the shaft 14. The outer diameter of the ring member 100 is slightly smaller than the inner diameter path followed by the radially innermost surface of the fixed stop 70 to provide sufficient clearance between the ring member 100 and the fixed stop 70 for free rotation of the ring member 100 about the shaft 14.

The radially outward protruding member 80 of the free rotating ring 60 may include a tab 80, wherein the first and second contact faces 82, 84 are on opposite peripheral sides of the tab 80. The ring member 100 may include a radial opening 190 to accommodate the tab 80. The tab 80 and radial opening 190 protrude radially relative to the rotation axis A-A, that is, radially from the geometric center of the free rotating ring 60. As shown in FIGS. 8-10, the tab 80 and radial opening 190 have a constant width in the radial direction. The width of the tab 80 is slightly less than the width of the radial opening 190 to enable the tab 80 to be radially slidably inserted into, or withdrawn from, the radial opening 190. The tab 80 is inserted into the radial opening 190 in the ring member 100 such that the tab 80 protrudes radially outward relative to the outer diameter of the ring member 100 yet does not protrude radially inward relative to the inner diameter of the ring member 100. The amount of radially outward protrusion is such that the first and second contact faces 82, 84 of the tab 80 are located the same radial distance from the rotation axis A-A (or on the same circumference) as the first and second contact faces 72, 74 of the fixed stop 70, and thus in operation abuttingly engage the respective first and second contact faces 72, 74. As shown in FIG. 10, a fastener such as a screw 192 may be fastened into a threaded opening 194 in the tab 80 to secure the tab 80 to the ring member 100 and within the radial opening 190. In some embodiments, the screw 192 may additionally be secured in the threaded opening 194 by a suitable thread locking adhesive.

The radially inward protruding member 90 may include a fastener such as screw 90, wherein the first and second contact faces 92, 94 are on opposite peripheral sides of the screw 90. The ring member 100 may include a radial opening 210 to accommodate the screw 90. The screw 90 and radial opening 210 protrude radially relative to the rotation axis A-A, that is, radially from the geometric center of the free rotating ring 60. As shown in FIGS. 8-10, the radial opening 210 includes a radially inner through hole 212, a radially outer threaded hole 214, and an intermediate annular seat 216, while the screw 90 in a corresponding manner includes a radially inner shaft 232, a radially outer threaded socket head 234, and an intermediate annular flange 236. The threaded socket head 234 of the screw 90 is threaded into the threaded hole 214 of the radial opening 210 until the annular flange 236 engages, i.e. rests on, the annular seat 216, which results in the shaft 232 extending through the through hole 212 and protruding radially inward relative to the inner diameter of the ring member 100. The screw 90 also does not protrude radially outward relative to the outer diameter of the ring member 100. The amount of radially inward protrusion is such that the first and second contact faces 92, 94 of the radially inward protruding member 90 are at the same radial distance from the rotation axis A-A (or on the same circumference) as the first and second contact faces 52, 54 of the elongated peripheral cavity 50, and thus in operation abuttingly engage the respective first and second contact faces 52, 54. In some embodiments, the screw 90 may additionally be secured in the threaded hole 214 of the radial opening 210 by a suitable thread locking adhesive.

In the illustrative rotational control mechanism 40, there are three radially inward protruding members 90 and three corresponding elongated peripheral cavities 50 within which the radially inward protruding members 90 respectively move during rotation of the extension arm 16 about the shaft 14. As shown in FIGS. 5-7 and 9 the three elongated peripheral cavities 50 and the three radially inward protruding members 90 are evenly spaced about the rotation axis A-A of the shaft 14. In the illustrative embodiment, the even spacing is an angular spacing of 120° (120 degrees) between adjacent elongated peripheral cavities 50 and an angular spacing of 120° (120 degrees) between adjacent radially inward protruding members 90. It will be appreciated that one or more elongated peripheral cavities 50 and one or more radially inward protruding members 90 may be suitable for the rotational control mechanism 40. For example, in some embodiments there may be one elongated peripheral cavity 50 and one radially inward protruding member 90. In other embodiments, there may be, two, four, etc. Further, the number of elongated peripheral cavities 50 need not be the same as the number of radially inward protruding members 90. For example, there may be three elongated peripheral cavities 50 and only one radially inward protruding member 90 in which case two of the elongated peripheral cavities 50 may go unused during operation but would provide flexibility in assembly of the extension arm 16 to the shaft 14 and integration of the rotational control mechanism 40 into the hub 34.

FIGS. 3-7 and 11-14 show greater detail of the fixed stop 70 of the rotational control mechanism 40. The fixed stop 70 may include a block 70 with beveled edges forming the respective first and second contact faces 72, 74 on opposite peripheral sides of the block 70. The fixed stop 70 may include a threaded opening at its center that is alignable with a through hole in a wall 264 of the hub 34. A fastener 270 may be inserted through the through hole and threaded into the threaded opening to secure the block 70 to a radially inward facing portion 280 of the wall 264 of the hub 34. In some embodiments, the fastener 270 may additionally be secured in the threaded opening by a suitable thread locking adhesive. As shown in FIGS. 3, 5-7 and 11-14, the fixed stop 70, when fastened to the wall 264, protrudes axially downward from its fastener location, which positions the fixed stop 70 and its first and second contact faces 72, 74 at the same axial location as the radially outward protruding member 80 and its first and second contact faces 82, 84.

Figure 14:
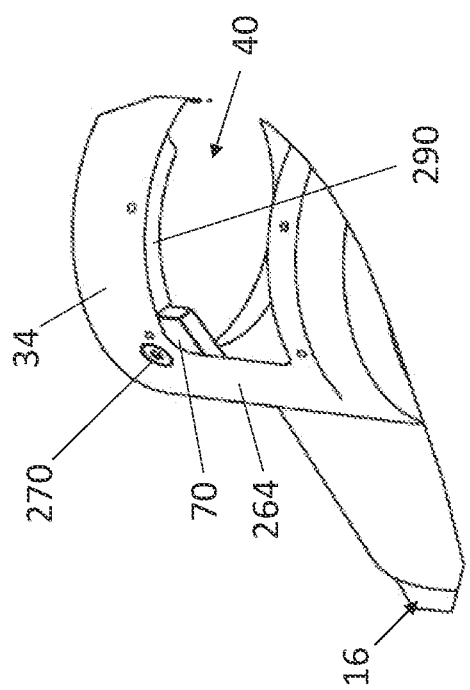
FIG. 14 is a view similar to the FIG. 13 view but from an opposite side of the hub.
Figure 13:
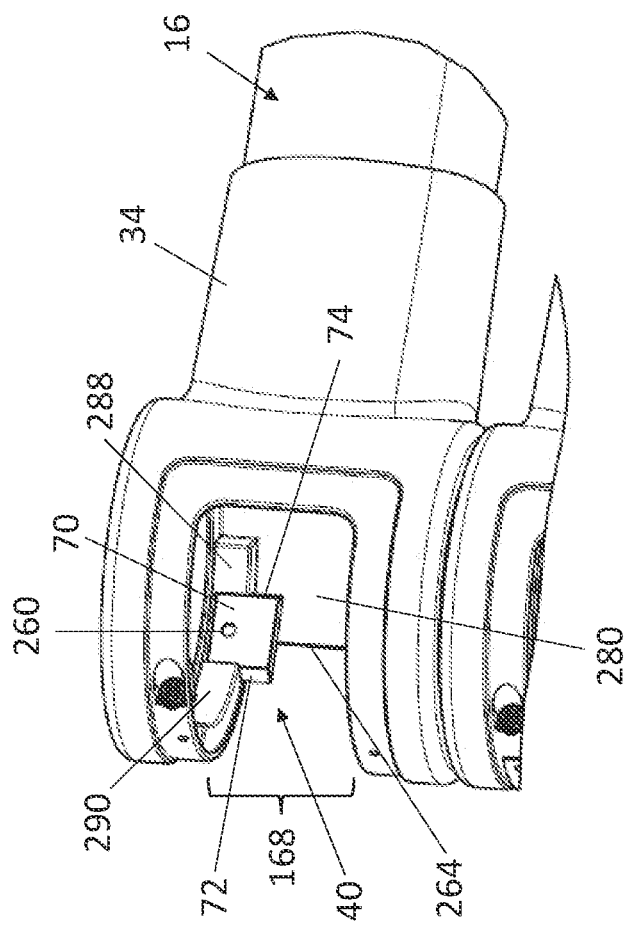
FIG. 13 is an isometric view of the FIGS. 11 and 12 shaft and extension arm hub connection but omitting a free rotating ring and shaft to more clearly show the fixed stop.

With continued reference to FIGS. 13 and 14, the fixed stop 70 may additionally be secured at its opposite peripheral sides by radially inward protruding walls or castings 288, 290 of the hub 34.

Referring now to FIGS. 5-7, the amount of radially outward protrusion of the radially outward protruding member 80 relative to the ring member 100, more particularly the outer diameter of the ring member 100, is such that the first and second contact faces 82, 84 of the radially outward protruding member 80 are at the same radial distance from the rotation axis A-A (or on the same circumference) as the first and second contact faces 72, 74 of the fixed stop 70, and thus in operation abuttingly engage the respective first and second contact faces 72, 74.

Turning now to FIGS. 3-7 and 10-12, in the illustrative embodiment, the radially outward protruding member 80 of the free rotating ring 60 and the radially inward protruding member 90 of the free rotating ring 60 lie in the same plane and the plane is perpendicular to the rotation axis A-A. In this way, the rotational control mechanism 40 embodies fewer components and a smaller volumetric footprint than heretofore attained and simplifies and adds efficiency to the factory assembly and field service of the medical device support system 10. Also, the radially outward protruding member 80 of the free rotating ring 60 and the elongated peripheral cavity 50 of the shaft 14 lie in the same plane and the plane is perpendicular to the rotation axis A-A. Thus, in the embodiment of FIGS. 3-7 and 10-12, the radially outward protruding member 80, the radially inward protruding member 90, and the elongated peripheral cavity 50 lie in the same plane perpendicular to the rotation axis A-A. Of course, the invention need not be limited as such and other embodiments are contemplated. For example, the radially outward protruding member 80 may be located in a plane axially above or axially below the plane in which the radially inward protruding member 90 and the elongated peripheral cavity 50 lie. In another example, the radially outward protruding member 80 may be located in a plane axially above or axially below the plane in which the radially inward protruding member 90 lies, and the elongated peripheral cavity 50 may have an axial height such that the radially outward protruding member 80 and the radially inward protruding member 90, although themselves in different planes, both lie in the axial height plane of the elongated peripheral cavity 50.

In the illustrative embodiment, the fixed stop 70 of the hub 34 and the radially inward protruding member 90 of the free rotating ring 60 lie in the same plane and the plane is perpendicular to the rotation axis A-A. In this way, the rotational control mechanism 40 embodies fewer components and a smaller volumetric footprint than heretofore attained and simplifies and adds efficiency to the factory assembly and field service of the medical device support system 10. Also, fixed stop 70 of the hub 34 and the elongated peripheral cavity 50 of the shaft 14 lie in the same plane and the plane is perpendicular to the rotation axis A-A. Thus, in the embodiment of FIGS. 3-7 and 10-12, the fixed stop 70, the radially inward protruding member 90, and the elongated peripheral cavity 50 lie in the same plane perpendicular to the rotation axis A-A. Of course, the invention need not be limited as such and other embodiments are contemplated. For example, the fixed stop 70 may be located in a plane axially above or axially below the plane in which the radially inward protruding member 90 and the elongated peripheral cavity 50 lie. In another example, the fixed stop 70 may be located in a plane axially above or axially below the plane in which the radially inward protruding member 90 lies, and the elongated peripheral cavity 50 may have an axial height such that the fixed stop 70 and the radially inward protruding member 90, although themselves in different planes, both lie in the axial height plane of the elongated peripheral cavity 50.

In the illustrative embodiment, the radially outward protruding member 80, the radially inward protruding member 90, the elongated peripheral cavity 50, and the fixed stop 70 all lie in the same plane perpendicular to the rotation axis A-A. In this way, the rotational control mechanism 40 embodies fewer components and a smaller volumetric footprint than heretofore attained and simplifies and adds efficiency to the factory assembly and field service of the medical device support system 10.

Figure 15:
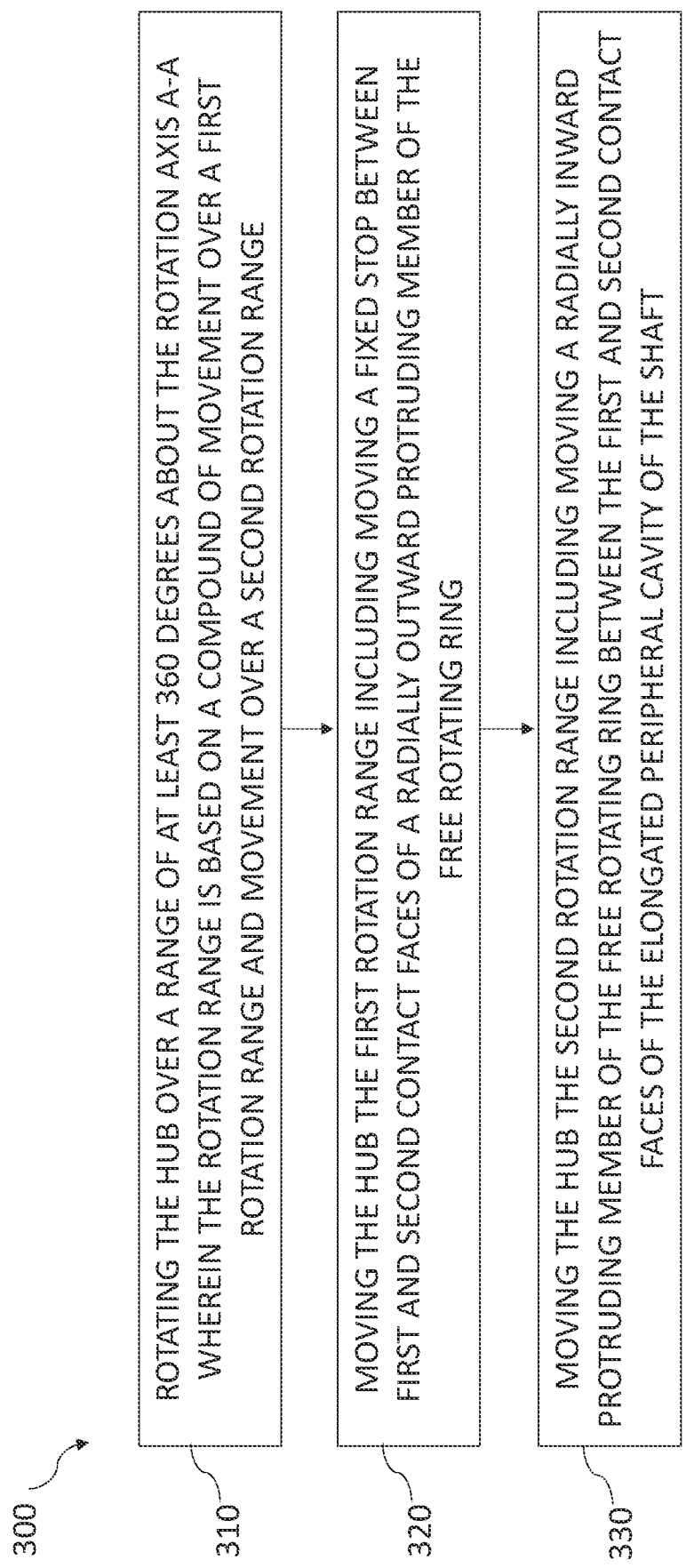
FIG. 15 shows a flowchart of a method of rotating an extension arm about a shaft of a medical device support system in accordance with an embodiment of the invention.

Referring now to FIG. 15, there is shown a flowchart 300 of a method of rotating an extension arm 16 about a shaft 14 of a medical device support system 10 such as shown in FIG. 1. The extension arm 16 has a support 20 for a medical device 30 and a hub 34 at its proximal end mounted to the shaft 14 for pivotable movement about a rotation axis A-A of the shaft 14. A free rotating ring 60 is rotatable about the rotation axis A-A and is movable relative to the shaft 14 and movable relative to the hub 34. The shaft 14 includes at least one elongated peripheral cavity 50 that defines first and second contact faces 52, 54 at opposite peripheral ends of the cavity 50. The method includes at step 310 rotating the hub 34 over a range of at least 360° (360 degrees) about the rotation axis A-A, wherein the at least 360° (360 degrees) rotation range is based on a compound of movement over a first rotation range and movement over a second rotation range. At step 320, the movement over the first rotation range includes moving a fixed stop 70 of the hub 34 between first and second contact faces 72, 74 of a radially outward protruding member 80 of the free rotating ring 60. At step 330, the movement over the second rotation range includes moving a radially inward protruding member 90 of the free rotating ring 60 between the first and second contact faces 52, 54 of the elongated peripheral cavity 50 of the shaft 14.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A medical device support system, comprising:
a shaft;
an extension arm having a support for a medical device and a hub at its proximal end mounted to the shaft for pivotable movement about a rotation axis of the shaft;
a free rotating ring that is rotatable about the rotation axis and is movable relative to the shaft and movable relative to the hub;
wherein the shaft includes at least one elongated peripheral cavity that defines first and second contact faces at opposite peripheral ends of the cavity;
wherein the hub is pivotably mounted for a range of at least 360° (360 degrees) rotation about the rotation axis, wherein the at least 360° (360 degrees) rotation range is based on a compound of a first rotation range and a second rotation range, wherein the first rotation range is defined by a fixed stop of the hub configured to move between first and second contact faces of a radially outward protruding member of the free rotating ring, wherein the second rotation range is defined by a radially inward protruding member of the free rotating ring configured to move between the first and second contact faces of the elongated peripheral cavity of the shaft.

2. The medical device support system of claim 1, wherein the free rotating ring is configured to prevent rotation of the hub about the rotation axis beyond the at least 360° (360 degrees) rotation range.

3. The medical device support system of claim 1, wherein the hub is pivotably mounted for at least 360° (360 degrees) rotation from a first stop to a second stop and vice versa, wherein the first stop limits counterclockwise rotation of the hub about the rotation axis and the second stop limits clockwise rotation of the hub about the rotation axis.

4. The medical device support system of claim 3, wherein the first stop includes the fixed stop of the hub in engagement with the first contact face of the radially outward protruding member of the free rotating ring, and the radially inward protruding member of the free rotating ring in engagement with the first contact face of the elongated peripheral cavity of the shaft.

5. The medical device support system of claim 3, wherein the second stop includes the fixed stop of the hub in engagement with the second contact face of the radially outward protruding member of the free rotating ring, and the radially inward protruding member of the free rotating ring in engagement with the second contact face of the elongated peripheral cavity of the shaft.

6. The medical device support system of claim 1, wherein the radially outward protruding member of the free rotating ring and the radially inward protruding member of the free rotating ring lie in the same plane and the plane is perpendicular to the rotation axis.

7. The medical device support system of claim 1, wherein the fixed stop of the hub and the radially inward protruding member of the free rotating ring lie in the same plane and the plane is perpendicular to the rotation axis.

8. The medical device support system of claim 1, wherein the radially outward protruding member of the free rotating ring includes a tab, and the first and second contact faces of the radially outward protruding member of the free rotating ring are on opposite peripheral sides of the tab.

9. The medical device support system of claim 8, wherein the free rotating ring includes a ring member and the tab is secured within a radial opening in the ring member.

10. The medical device support system of claim 1, wherein the radially inward protruding member of the free rotating ring has first and second contact faces on opposite sides thereof, and wherein the second rotation range is defined by movement of the radially inward protruding member between a location at which the first contact face of the radially inward protruding member engages the first contact face of the elongated peripheral cavity of the shaft and a location at which the second contact face of the radially inward protruding member engages the second contact face of the elongated peripheral cavity of the shaft.

11. The medical device support system of claim 1, wherein the free rotating ring includes a ring member, and the radially inward protruding member of the free rotating ring includes a fastener threaded into an opening in the ring member, and the fastener protrudes radially inward relative to an inner diameter of the ring member.

12. The medical device support system of claim 1, wherein the at least one elongated peripheral cavity includes a plurality of elongated peripheral cavities.

13. The medical device support system of claim 12, wherein the radially inward protruding member of the free rotating ring includes a plurality radially inward protruding members that move within the respective plurality of elongated peripheral cavities.

14. The medical device support system of claim 12, wherein the plurality of elongated peripheral cavities are evenly spaced about the rotation axis of the shaft.

15. The medical device support system of claim 1, wherein the shaft has an axial hollow and a radial aperture and wherein the free rotating ring is positioned to allow passage of electrical and communication lines through the axial hollow, through the free rotating ring, through the radial aperture, and into a longitudinally extending cavity in the extension arm.

16. The medical device support system of claim 15, wherein the hub of the extension arm includes upper and lower pivot bearings configured to pivotably engage the hub with the shaft, and a radial opening positioned axially between the upper and lower pivot bearings, and wherein the free rotating ring is positioned to allow passage of the electrical and communication lines between the upper and lower pivot bearings, through the radial opening of the hub, and into the longitudinally extending cavity in the extension arm.

17. A medical device support system, comprising:
a shaft;
an extension arm having a support for a medical device and a hub at its proximal end mounted to the shaft for pivotable movement about a rotation axis of the shaft;
a free rotating ring that is rotatable about the rotation axis and is movable relative to the shaft and movable relative to the hub;
wherein the shaft includes at least one elongated peripheral cavity that defines first and second contact faces at opposite peripheral ends of the cavity;
wherein the hub is pivotably mounted for a range of at least 360° (360 degrees) rotation about the rotation axis from a first stop to a second stop and vice versa, wherein the first stop limits counterclockwise rotation of the hub about the rotation axis and the second stop limits clockwise rotation of the hub about the rotation axis,
wherein the first stop includes a radially inward protruding member of the free rotating ring in engagement with the first contact face of the elongated peripheral cavity of the shaft, and wherein the second stop includes the radially inward protruding member of the free rotating ring in engagement with the second contact face of the elongated peripheral cavity of the shaft.

18. The medical device support system of claim 17, wherein the hub includes a fixed stop movable between first and second contact faces of a radially outward protruding member of the free rotating ring.

19. The medical device support system of claim 18, wherein the first stop includes the fixed stop of the hub in engagement with the first contact face of the radially outward protruding member of the free rotating ring, and wherein the second stop includes the fixed stop of the hub in engagement with the second contact face of the radially outward protruding member of the free rotating ring.

20. A method of rotating an extension arm about a shaft of a medical device support system, the extension arm having a support for a medical device and a hub at its proximal end mounted to the shaft for pivotable movement about a rotation axis of the shaft, wherein a free rotating ring is rotatable about the rotation axis and is movable relative to the shaft and movable relative to the hub, and wherein the shaft includes at least one elongated peripheral cavity that defines first and second contact faces at opposite peripheral ends of the cavity, the method comprising:
rotating the hub over a range of at least 360° (360 degrees) about the rotation axis, wherein the at least 360° (360 degrees) rotation range is based on a compound of movement over a first rotation range and movement over a second rotation range,
wherein movement over the first rotation range includes moving a fixed stop of the hub between first and second contact faces of a radially outward protruding member of the free rotating ring, and
wherein movement over the second rotation range includes moving a radially inward protruding member of the free rotating ring between the first and second contact faces of the elongated peripheral cavity of the shaft.

* * * * *